United States Patent [19]

Hilbert et al.

[11] 4,372,891

[45] Feb. 8, 1983

[54] METHOD OF RECOVERING PURE TOLUENE DIISOCYANATE FROM A POLYMERIC RESIDUE PRODUCT

[76] Inventors: Lloyd E. Hilbert, Kanawha Ter., St. Albans, W. Va. 25177; Randall H. Samples, 1912 Springs Rd., Mt. Airy, N.C. 27030

[21] Appl. No.: 750,901

[22] Filed: Dec. 15, 1976

Related U.S. Application Data

[63] Continuation of Ser. No. 74,934, Sep. 23, 1970, abandoned.

[51] Int. Cl.³ .......................................... C07C 119/048
[52] U.S. Cl. .............................................. 260/453 SP
[58] Field of Search ................................ 260/453 SP

[56] References Cited

U.S. PATENT DOCUMENTS 3,144,474  8/1964  Kantyka et al. .............. 260/453 SP
3,211,631  10/1965  Fuchs ............................ 260/453 SP
3,479,384  11/1969  Heiss ............................. 260/453SP

*Primary Examiner*—Dolph H. Torrence
*Attorney, Agent, or Firm*—Buell, Blenko, Ziesenheim & Beck

[57] ABSTRACT

Polymeric residue including toluene diisocyanate is combined with a solvent having a low affinity for polymer solution and a high affinity for toluene diisocyanate to dissolve toluene diisocyanate leaving the polymeric materials in suspension. The polymeric compounds are precipitated and filtered, the filtrate solution distilled and the toluene diisocyanate recovered as a pure product.

8 Claims, No Drawings

METHOD OF RECOVERING PURE TOLUENE DIISOCYANATE FROM A POLYMERIC RESIDUE PRODUCT

This application is a continuation of our copending application Ser. No. 74,934, filed Sept. 23, 1970, abandoned.

BRIEF SUMMARY AND OBJECTS OF THE INVENTION

This invention relates to the recovery of toluene diisocyanate, and more particularly to a method for recovering pure toluene diisocyanate from a residue product which remains after the original manufacturing process of producing toluene diisocyanate.

Polymeric materials produced by such process are miscible with toluene diisocyanate and cling to it so tenaciously that it is extremely difficult or impractical to remove by distillation to concentrations of less than approximately 50%-60% toluene diisocyanate. The residue becomes so viscous and tar-like that further evaporation is impractical. All manufacturers of toluene diisocyanate are confronted with this residue problem regardless of the process used for the production of toluene diisocyanate. While this residue product containing toluene diisocyanate and polymeric materials may be satisfactory in certain foaming operations such as cavity insulation, etc., where color and certain other physical properties are not important, such a residue product is considerably inferior to pure toluene diisocyanate.

Briefly, the present invention involves a process wherein pure toluene diisocyanate can be recovered from a polymeric residue product which remains after the original toluene diisocyanate manufacturing process, by extracting with a solvent composition such that toluene diisocyanate is dissolved leaving the polymeric materials in suspension as a particulate solid which is readily filterable. The filtrate then can be distilled to recover pure toluene diisocyanate and regain the solvent composition for recycle.

One of the primary objects of the invention is a process for recovering pure toluene diisocyanate from a residue product.

Another object of the invention is the provision of an economically practical and simple method for rapidly recovering toluene diisocyanate from a polymeric residue.

A further object of the invention is the provision of a solvent having a low affinity for polymer solvation and a high affinity for toluene diisocyanate for extracting toluene diisocyanate from a polymeric residue product.

Other objects, advantages and features of the invention will become apparent from the following description.

In general, the subject invention comprises the discovery that toluene diisocyanate can be recovered from polymeric residue product by extraction with a properly selected solvent. Such a solvent would of necessity have a low affinity for polymer solvation and yet have a high affinity for toluene diisocyanate. Thus the polymeric compounds could be precipitated and filtered. The filtrate containing the toluene diisocyanate in solution then can be distilled and the toluene diisocyanate recovered as a pure product. Approximately 95% of the toluene diisocyanate contained in the residue can be recovered in this manner.

The composition and molecular weight range of the solvent must be such as to achieve the desired compromise between its affinity for toluene diisocyanate and for the polymeric material. The polymer is an aromatic in nature and of high molecular weight whereas the toluene diisocyanate is also aromatic but of much lower molecular weight. Aromatic solvents, such as benzene, toluene or xylene, or chlorinated solvents, such as dichlorobenzene, methylene chloride or ethylene dichloride, are undesirable because they dissolve not only the toluene diisocyanate but also most of the polymer material. In contrast, an aliphatic is undesirable since it appears to have a high affinity for the toluene diisocyanate but leaves enough toluene diisocyanate with the polymer material to make a viscous tar-like mass.

By experiment, it has been found that a low boiling range aliphatic hydrocarbon in the molecular weight range between dodecane and hexane is a desirable aliphatic component of a solvent for extracting toluene diisocyanate. If toluene diisocyanate concentration is maintained high in the extract, the precipitated solids are particulate and filterable but if the concentration becomes low, for example, less than 10%, by using a greater ratio of aliphatic solvent to toluene diisocyanate residue, the polymeric layer left behind is no longer particulate but becomes a viscous sticky tar which is extremely difficult to handle by filtration. It has been found, for example, that a 1:1 or 2:1 ratio of toluene diisocyanate residue to an aliphatic will yield a particulate precipitate which is filterable whereas a ratio less than 1:10 will yield a solvent extract leaving behind a tacky tar which is difficult or impossible to handle by normal decantation or filtration procedures.

It becomes obvious that the ratio of aromatics or chlorinated solvents to aliphatics in the solvent mixture is of primary importance in the success of this process, whether the ratio be produced by a solvent mixture or by the extraction of toluene diisocyanate.

Therefore, an admixture of aromatics (or chlorinated hydrocarbons) and aliphatics becomes mandatory, with the selection of a boiling point range and composition of the admixture becoming a matter of economics. Both components of the admixture are physically and chemically operable over a wide range of composition but the two should have boiling points that are relatively close to each other in order to permit them to be separated by distillation as one solvent for recycle yet permit easy separation from the toluene diisocyanate. Another factor to consider in selecting the two components is the ease of separation from various other solvents utilized in the original manufacturing process of the toluene diisocyanate.

An example of such a solvent mixture which would satisfy all of the foregoing requirements is: xylene, an aromatic solvent having a mixed isomers-boiling point range of 137° C.–144° C., admixed with nonane or a mineral spirits aliphatic solvent having a boiling point range approximately that of the xylene mixed isomers. The ratio of aromatics to aliphatics between 90:10 and 10:90, and the ratio toluene diisocyanate residue product to the selected solvent mixture are not critical but should be determined on the basis of economics. However, it must be noted that toluene diisocyanate is an aromatic of still greater affinity for the polymeric material and must be considered in determining the actual ratio of aromatics to aliphatics in the solvent mixture when determining the amount of low molecular weight polymeric material which will be extracted.

Further, it has been found that chlorinated hydrocarbons, either as mixtures or individually, such as ethylenedichloride or dichlorobenzene, may be substituted entirely or in part for the aromatic portion of the solvent mixture whenever deemed desirable. Also, it is anticipated that low molecular weight compounds other than toluene diisocyanate but containing active isocyanate groups, such as dimers and trimers may be further isolated as useful products or possibly converted to toluene diisocyanate by depolymerization through mild pyrolysis either separately or by recycling through a toluene diisocyanate vacuum recovery distillation system.

A mobile liquid containing these low molecular weight polymers, for example, can be precipitated from the original extract by further dilution with the initial solvent mixture or with the pure aliphatic component. The immiscible liquid then can be separated and used, with or without further solvent removal, as a reactive isocyanate-containing material in the formulation of adhesives or further pyrolyzed to yield additional toluene diisocyanate and recycled through the extraction system.

In carrying out the novel process of this invention, the solvent is combined with the toluene diisocyanate residue product such that precipitation of the polymeric solids occurs in suspended particulate form and can be filtered with or without elutriation. Once the desirable toluene diisocyanate has been removed as a solution in the solvent mixture, to the practical exclusion of the polymeric solids, it can be recovered by a simple, conventional distillation process.

The solids collected during the filtering operation may be processed further to recover isocyanate-containing materials remaining therein, if desired.

We claim:

1. A method of recovering toluene diisocyanate from a residue product remaining after the original manufacturing process and resulting from the distillation of toluene diisocyanate down to levels of toluene diisocyanate where the residue in the original manufacturing process makes further evaporation impractical and containing residual toluene diisocyanate together with polymeric materials consisting essentially of the steps of: combining the residuel product with a solvent to dissolve the toluene diisocyanate while leaving the polymeric materials undissolved in suspension; said solvent consisting essentially of an aliphatic hydrocarbon in the molecular weight range between dodecane and hexane and a hydrocarbon from the group consisting of aromatic and chlorinated hydrocarbons having a boiling point approximating that of the said aliphatic hydrocarbon, the ratio of said aliphatic hydrocarbon to said aromatic hydrocarbons being in the range 90:10 and 10:90 and separating the dissolved toluene diisocyanate from the undissolved suspended polymeric materials by filtration.

2. The method of claim 1, wherein the toluene diisocyanate is substantially separated from the polymeric materials by filtration.

3. The method of claim 2, wherein the filtrate is distilled to recover substantially pure toluene diisocyanate.

4. The method of claim 2, wherein the polymeric materials are in particulate form and filtered.

5. The method of claim 1, wherein the solvent has a low affinity for polymer solvation and a high affinity for toluene diisocyanate.

6. The method of claim 1, wherein the solvent comprises an admixture of aromatic and aliphatic hydrocarbons such that toluene diisocyanate is dissolved and leaving the polymeric materials in suspension as a particulate solid.

7. The method of claim 6, wherein the boiling point range of the aromatics is substantially equal to that of the aliphatics.

8. The method of claim 1 wherein the solvent comprises a mixture of chlorinated hydrocarbons and aliphatic hydrocarbons.

* * * * *

UNITED STATES PATENT AND TRADEMARK OFFICE
CERTIFICATE OF CORRECTION

PATENT NO. : 4,372,891

DATED : February 8, 1983

INVENTOR(S) : Lloyd E. Hilbert and Randall H. Samples

It is certified that error appears in the above-identified patent and that said Letters Patent are hereby corrected as shown below:

Claim 1, column 4, line 5, "residuel" should be --residue--.

Signed and Sealed this

Twenty-first Day of June 1983

[SEAL]

Attest:

DONALD J. QUIGG

Attesting Officer

Acting Commissioner of Patents and Trademarks